United States Patent [19]

Chibnik

[11] 4,202,783
[45] May 13, 1980

[54] ANTIOXIDANT ADDITIVES AND LUBRICANT COMPOSITIONS CONTAINING SAME

[75] Inventor: Sheldon Chibnik, Cherry Hill, N.J.

[73] Assignee: Mobil Oil Corporation, New York, N.Y.

[21] Appl. No.: 937,667

[22] Filed: Aug. 28, 1978

[51] Int. Cl.² ............... C10M 1/20; C10M 1/32; C07D 249/18
[52] U.S. Cl. ............... 252/51.5 A; 252/403; 548/261
[58] Field of Search ............... 252/51.5 A, 403; 260/308 B

[56] References Cited

U.S. PATENT DOCUMENTS

| | | | |
|---|---|---|---|
| 3,791,803 | 2/1974 | Andress et al. | 44/63 |
| 4,048,082 | 9/1977 | Nnadi et al. | 252/392 X |

FOREIGN PATENT DOCUMENTS

390092  1/1974  U.S.S.R. ............... 260/308 B

*Primary Examiner*—W. J. Shine
*Attorney, Agent, or Firm*—Charles A. Huggett; Raymond W. Barclay; Howard M. Flournoy

[57] ABSTRACT

Benzotriazole when reacted with unsaturated esters such as acrylate ester provides products which when added to lubricating oils improve the resistance of said oils to oxidation.

22 Claims, No Drawings

ANTIOXIDANT ADDITIVES AND LUBRICANT COMPOSITIONS CONTAINING SAME

BACKGROUND OF THE INVENTION

1. Field of the Invention

This application relates to novel compounds prepared by reacting benzotriazole with an unsaturated ester and to antioxidant compositions comprising a major amount of, for example, an oil of lubricating viscosity and a minor effective amount of the above referred to benzotriazole/unsaturated ester adduct.

2. Summary of the Prior Art

The addition of benzotriazole to various conjugated systems via Michael addition has been reported in rather poor yield with acrylic acid, crotonic acid, cinnameldehyde, benzalacetophenone and maleic anhydride. The acrylonitrile adduct and esters of the maleic anhydride adduct are also known. The present work, however, is drawn to, e.g., acrylate and methacrylate ester adducts which can be prepared in high yield. A substantial amount of a 2-isomer product occurs. The mixture is useful as an antioxidant.

SUMMARY OF THE INVENTION

In accordance with the present invention it has now been found that the reaction of benzotriazole and an unsaturated ester, e.g., methacrylate ester, provides an adduct or benzotriazole complex having utility as an antioxidant additive.

More specifically this application is drawn to benzotriazole/unsaturated ester complexes and to antioxidnt lubricant compositions comprising a major proportion of lubricant medium normaly susceptible to oxidation and a minor effective proportion or mixture thereof of the herein described additive compounds.

A typical reaction in the equation shown below is with acrylate or methacrylate ester. A benzotriazole is reacted with an acrylate or methacrylate ester to form a mixture of isomers I and II, usually in about a 2/1 ratio with I predominant. The products are then added to the organic media, e.g., an oil of lubricating viscosity or a grease prepared therefrom to improve resistance of said oil or grease to oxidation.

The general reaction is as follows:

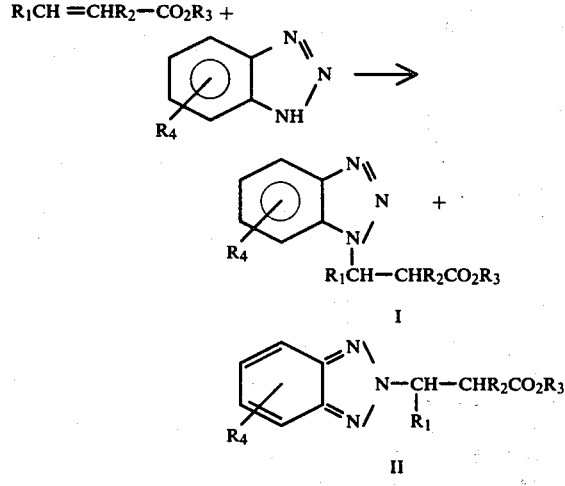

where $R_1$ and $R_2$=H or $C_1$ to $C_8$ alkyl, $R_3$=$C_2$ to $C_{22}$ or mixtures of $C_2$-$C_{22}$ and $R_4$=$CH_3$ or H. Additionally $R_3$ may also be selected from methyl, ethylhexyl, hydroxyethyl and tetraethyleneglycol acrylate.

The resultant adduct may be incorporated into a variety of organic mediums that are normally susceptible to oxidation. Especially preferred are oils of lubricating viscosity or greases derived therefrom and various functional fluids such as hydraulic fluids, transmission fluids, and power steering fluids. The antioxidant additives embodied herein in general are useful both in mineral oils and synthetic oils, mineral oil fractions and in combinations of mineral and synthetic oils.

Lubricant oils, improved in accordance with the present invention, may be of any suitable lubricating viscosity range, e.g., from about 45 SSU at 100° F. to about 6,000 SSU at 100° F., and preferably, from about 50 to 250 SSU at 210° F. Thus, oils having viscosity indexes from about 70 to about 95 are preferred. The average molecular weight of such oils may range from about 250 to about 800.

In instances where synthetic oils are desired in preference to mineral oils, they may be employed in lubricant compositions alone or as indicated above in combination with mineral oils. They may also be so used as the lubricant base or vehicle for grease compositions. Typical synthetic lubricants include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl esters typified by a butyl-substituted bis(p-phenoxy phenyl) ether, phenoxy phenyleters, etc.

For many applications the benzotriazole/unsaturated ester adduct may be present in an amount from about 0.001% to about 10 wt. % and preferably from about 0.05% to about 5 wt. % and more preferably from about 0.1% to about 1 wt. %, by weight of the total composition. Any other additive normally used in such media, e.g., a corrosion agent, may be used with these additive compounds without adverse effect.

DESCRIPTION OF SPECIFIC EMBODIMENTS

The following examples, remarks and comparative data will serve to illustrate more specifically preferred embodiments of the invention.

Referring back to the general reaction equation, the examples set forth below show $R_1$=H; for acrylates ($R_2$=H); and methacrylates ($R_2$=$CH_3$) with benzotriazole ($R_4$=H) and a commercial mixture of tolyltriazole ($R_4$=$CH_3$, substitution at positions 4 and 5 of the benzene ring). Similar results would be expected from crotonic acid esters ($R_1$=$CH_3$) or from triazole itself. $R_3$ has been illustrated from $C_2$ to $C_{12+}$; its nature is unimportant except to confer solubility.

EXAMPLE

Preparation of Additives

A solution of 31.3 g (0.31 moles) of ethyl acrylate, 36.5 g (0.31 moles) benzotriazole, 0.6 g potassium t-butoxide (catalyst) and 0.015 g phenyl α-naphthylamine (polymerization inhibitor) in t-butanol was refluxed overnight. The product was stripped of solvent by distillation, freed of catalyst by solution in hexane and water washing and finally stripped of hexane and any excess monomer by vacuum topping. Product yield was normally above 95%.

In some instances the solvent may simply be stripped; the small amount of catalyst can be tolerated for many uses and the amount of unreacted monomer is negligible in most cases. The solvent is not required and was omitted in the case of lauryl methacrylate where a temperature of 160° C. for 6 hours was necessary to obtain a 91% yield of benzotriazole adduct. With low molecular weight acrylate esters an 80% reaction was achieved in one hour under the cited conditions. At least 1 g catalyst/mole reactant is required for a 95% yield in 3 hours. If only 0.1 g catalyst is used the yield was only 55% in 5 hours. If the inhibitor is omitted some oligimers of the acrylate or adduct are formed.

Separation of isomers may be achieved by chromatography if desired.

Using the above ratios of materials (molar equivalents of acrylates and triazoles), the following preparations have been made:

| Example | $R_1$ | $R_2$ | $R_3$ | $R_4$ |
|---|---|---|---|---|
| 1 | H | $CH_3$ | $C_{12}$* | H |
| 2 | H | H | $C_8$** | H |
| 3 | H | H | $C_8$** | $CH_3$ |
| 4 | H | H | $C_4$ | H |
| 5 | H | H | $C_2$ | $CH_3$ |
| 6 | H | $CH_3$ | HE | H |
| 7 | H | H | TEGA | H |
| 8 | H | H | $C_2$ | H |

*Commercial mixture of $C_{10}$—$C_{20}$, mainly $C_{12}$
**2-Ethylhexyl
HE = Hydroxyethyl
TEG = Tetraethyleneglycol acrylate (from TEG diacrylate)

Some representative additives prepared in accordance with the above exemplary data were then evaluated for antioxidant effectiveness in a standard oxidation test.

CATALYTIC OXIDATION TEST

A sample of the base lubricant is placed in an oven at a desired temperature. Present in the sample are the following metals either known to catalyze organic oxidation or commonly used materials of construction.
a. 15.6 sq. in. of sand-blasted iron wire,
b. 0.78 sq. in. of polished copper wire,
c. 0.87 sq. in. of polished aluminum wire, and
d. 0.167 sq. in. of polished lead surface.
Dry air is passed through the sample at a rate of about 5 liters per hour.

The data from this test are recorded below in the Table. This data illustrates the unexpected and surprising superiority of compounds in accordance with this invention over the prior art.

A 1% solution of the test sample in a 100 sec solvent refined mineral oil was subject to the above catalytic oxidation test procedure at 325° F. for 40 hours with the following results:

| Example | Acid Value Increase, mg KOH/g | % Viscosity Increase | mg. Pb Loss |
|---|---|---|---|
| Control, no additive | 17 | 334 | 171.3 |
| 2 | 9.6 | 45.9 | 0.6 |
| 8 | 9.1 | 74.4 | 0.7 |
| 3 | 11.0 | 78.8 | 3.3 |

-continued

| Example | Acid Value Increase, mg KOH/g | % Viscosity Increase | mg. Pb Loss |
|---|---|---|---|
| 1 | 7.1 | 42.0 | 13.7 |

While the present invention has been described with reference to preferred embodiments (including compositions and components), it will be readily understood by those skilled in the art that departure from such embodiments can be effectively made within the scope of this specification.

What is claimed is:

1. A compound or mixture of compounds prepared by reacting under suitable conditions a benzotriazole and an unsaturated ester and thereafter recovering as final product

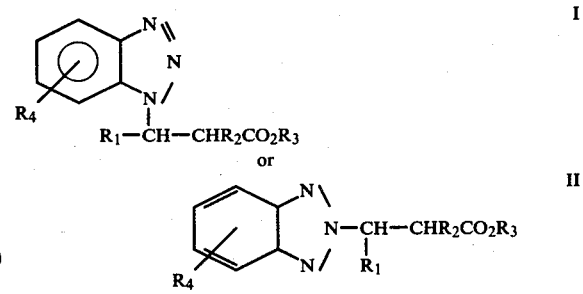

or mixtures thereof where $R_1$ and $R_2$=H or $C_1$ to $C_8$ alkyl and $R_3$ is selected from methyl, ethylhexyl, hydroxyethyl and tetraethylenegycol acrylate, and $C_2$ to $C_{22}$ or mixtures of $C_2$–$C_{22}$ and $R_4$=H or $CH_3$.

2. The compounds of claim 1 where $R_1$=H, $R_2$=$CH_3$, $R_3$=$C_{12}$ or a mixture of $C_{10-20}$ which is primarily $C_{12}$ and $R_4$=H.

3. The compounds of claim 1 where $R_1$ and $R_2$=H, $R_3$=$C_8$ and $R_4$=H.

4. The compounds of claim 1 where $R_1$ and $R_2$=H, $R_3$=$C_8$ and $R_4$=$CH_3$.

5. The compounds of claim 1 where $R_1$ and $R_2$=H, $R_3$=$C_4$ and $R_4$=H.

6. The compounds of claim 1 where $R_1$ and $R_2$=H, $R_3$=$C_2$ and $R_4$=$CH_3$.

7. The compounds of claim 1 where $R_1$=H, $R_2$=$CH_3$, $R_3$=hydroxyethyl and $R_4$=H.

8. The compounds of claim 1 where $R_1$ and $R_2$=H, $R_3$=tetraethyleneglycol acrylate and $R_4$=H.

9. The compounds of claim 1 where $R_1$ and $R_2$=H, $R_3$=$C_2$ and $R_4$=H.

10. An antioxidant lubricant composition comprising a major proportion of lubricant medium normally susceptible to oxidation and a minor effective proportion of an additive compound or mixture of such compounds as described in claim 1.

11. The composition of claim 10 where $R_1$=H, $R_2$=$CH_3$, $R_3$=$C_{12}$, or a mixture of $C_{10-20}$ which is primarily $C_{12}$, and $R_4$=H.

12. The composition of claim 10 where $R_1$ and $R_2$=H, $R_3$=$C_8$ and $R_4$=H.

13. The composition of claim 10 where $R_1$ and $R_2$=H, $R_3$=$C_8$ and $R_4$=$CH_3$.

14. The composition of claim 10 where $R_1$ and $R_2$=H, $R_3$=$C_4$ and $R_4$=H.

15. The composition of claim 10 where $R_1$ and $R_2=H$, $R_3=C_2$ and $R_4=CH_3$.

16. The composition of claim 10 where $R_1=H$, $R_2=CH_3$, $R_3=$hydroxyethyl and $R_4=H$.

17. The composition of claim 10 where $R_1$ and $R_2=H$, $R_3=$tetraethyleneglycol acrylate and $R_4=H$.

18. The composition of claim 10 where $R_1$ and $R_2=H$, $R_3=C_2$ and $R_4=H$.

19. The composition of claim 10 wherein the lubricant medium is selected from the group consisting of oils of lubricating viscosity or greases prepared therefrom and hydraulic fluids, transmission fluids and power steering fluids.

20. The composition of claim 19 wherein the lubricant medium is an oil of lubricating viscosity.

21. The composition of claim 20 wherein the oil of lubricating viscosity is a mineral oil.

22. The composition of claim 20 wherein the oil of lubricating viscosity is a synthetic oil.

* * * * *